United States Patent
Verwaal et al.

(10) Patent No.: US 9,556,459 B2
(45) Date of Patent: *Jan. 31, 2017

(54) DICARBOXYLIC ACID PRODUCTION IN A RECOMBINANT YEAST

(71) Applicant: DSM IP ASSETS B.V., Heerlen (NL)

(72) Inventors: Rene Verwaal, Echt (NL); Liang Wu, Echt (NL); Robbertus Antonius Damveld, Echt (NL); Cornelis Maria Jacobus Sagt, Echt (NL)

(73) Assignee: DSM IP ASSETS B.V., Heerlen (NL)

( * ) Notice: Subject to any disclaimer, the term of this patent is extended or adjusted under 35 U.S.C. 154(b) by 0 days.

This patent is subject to a terminal disclaimer.

(21) Appl. No.: 14/070,770

(22) Filed: Nov. 4, 2013

(65) Prior Publication Data

US 2014/0065680 A1 Mar. 6, 2014

Related U.S. Application Data

(63) Continuation of application No. 12/743,652, filed as application No. PCT/EP2008/065587 on Nov. 14, 2008.

(30) Foreign Application Priority Data

Nov. 20, 2007 (EP) .................................... 07121117
May 27, 2008 (EP) .................................... 08156960

(51) Int. Cl.
*C12P 7/46* (2006.01)
*C12N 9/88* (2006.01)

(52) U.S. Cl.
CPC . *C12P 7/46* (2013.01); *C12N 9/88* (2013.01); *Y02P 20/52* (2015.11)

(58) Field of Classification Search
None
See application file for complete search history.

(56) References Cited

U.S. PATENT DOCUMENTS

| 4,828,993 | A | 5/1989 | Sridhar |
| 5,643,758 | A | 7/1997 | Guan et al. |
| 8,735,112 | B2* | 5/2014 | Verwaal et al. ............. 435/145 |
| 2006/0246560 | A1 | 11/2006 | Fatland-Bloom et al. |
| 2007/0042477 | A1* | 2/2007 | Lee et al. ..................... 435/145 |

FOREIGN PATENT DOCUMENTS

| EP | 1 672 077 | 6/2006 |
| EP | 1867727 | 12/2007 |
| WO | 2006083410 | 8/2006 |
| WO | 2007/030830 | 3/2007 |
| WO | 2007/061590 | 5/2007 |
| WO | 2007/019301 | 7/2007 |
| WO | 2008144626 | 11/2008 |
| WO | 2009011974 | 1/2009 |

OTHER PUBLICATIONS

Chica et al. Curr Opin Biotechnol. Aug. 2005;16(4):378-84.*
Sen et al. Appl Biochem Biotechnol. Dec. 2007;143(3):212-23.*
Abe et al. (Mycopath. 2006, vol. 162, pp. 143-153).
Fujimaki et al., "Processability and properties of aliphatic polyesters, 'Bionolle', synthesized by polycondensation reaction", Polymer Degradation and Stability, Barking, GB vol. 59, No. 1-3, Jan. 3, 1998, pp. 209-214, XP027153158, ISSN: 0141-3910.
European Search Report corresponding to European Patent Application No. 13170415.7 dated Jan. 7, 2014.
May et al., "The Importance of Fungi to Man", Genome Research, (1997), vol. 7, pp. 1041-1044.
Wakai et al., "Formation of succinate during fermentation of sake mash and grape must", Brewing Technology (1980), 2 vol. 58, No. 5, pp. 363-368 [Japanese Original and English Translation] .
Flores et al., "Carbohydrate and energy-yielding metabolism in non-conventional yeasts", FEMS Microbiology Reviews, (2000), vol. 24, pp. 507-529.
Karniely et al., "Single translation-dual destination: mechanisms of dual protein targeting in eukaryotes", EMBO Reports, (2005) vol. 6., No. 5, pp. 420-425.
Nobel et al., Protein promiscuity and its implications for biotechnology, Nature Biotechnology, (Feb. 9, 2009), vol. 27, No. 2, pp. 157-167.
Vallon et al., "New Sequence Motifs in Flavoproteins: Evidence for Common Ancestry and Tools to Predict Structure", (2000), Proteins: Structure, Function and Genetics, vol. 38, pp. 95-114.
Camarasa et al., Role in anaerobiosis of the isoenzymes for *Saccharomyces cerevisiae* fumarate reductase encoded by OSM1 and FRDS1, Wiley Interscience, Mar. 7, 2007, pp. 391-401, Sciences pour l'Oenologie, INRA, Montpellier, France.
Patil et al., "Evolutionary programming as a platform for in silico metabolic engineering" BMC Bioinformatics. Dec. 23, 2005; 6:308.
Warnecke et al., Organic acid toxicity, tolerance, and production in *Escherichia coli* biorefining applications. Microb. Cell Fact. 4:25. 2005.
Romanos et al., Foreign Gene Expression in Yeast: A Review. Yeast vol. 8:423-488 (1992).
Stewart et al. Biotechnology and Genetic Engineering Reviews, 14:67-143, 1997.
UnitProt Database—retrieved from the Internet via http://www.uniprot.org on Feb. 11, 2013.
Q6w6x5-UniProtKB/TrEMBL Database 2007.
Accession P55250. Oct. 1, 1996.
International Search Report for PCT/EP2008/065587, mailed Feb. 12, 2009.
Written Opinion of the International Searching Authority for PCT/EP2008/065587, mailed Feb. 12, 2009.

(Continued)

*Primary Examiner* — Christian Fronda
(74) *Attorney, Agent, or Firm* — McBee Moore Woodward & Vanik IP, LLC

(57) ABSTRACT

The present invention relates to a recombinant yeast comprising a nucleotide sequence encoding a heterologous enzyme that catalyses the conversion of malic acid to fumaric acid. The invention further relates to a process for the production of a dicarboxylic acid wherein the yeast according to the present invention is used.

16 Claims, 2 Drawing Sheets

(56) References Cited

OTHER PUBLICATIONS

Goldberg et al., "Organic Acids: Old Metabolites, New Themes", Journal of Chemical Technology and Biotechnology, vol. 81, No. 10, Oct. 2006, pp. 1601-1611, XP002477014.
Pines et al., "The Cytosolic Pathway of L-malic Acid Synthesis in *Saccharomyces cerevisiae*: The Role of Fumarase", Applied Microbiology and Biotechnology, vol. 46, No. 4, 1996, pp. 393-399, XP008090537.
Peleg et al., "Inducible Overexpression of the FUM1 Gene in *Saccharomyces cerevisiae*: Localization of Fumarase and Efficient Fumaric Acid Bioconversion to L-malic Acid", Applied and Environmental Microbiology, vol. 56, 1990, pp. 2777-2783, XP002408560.
Friedberg et al., "The FumR gene Encoding Fumarase in the Filamentous Fungus Rhizopus Oryzae: Cloning, Structure and Expression" Gene, vol. 163, No. 1, Sep. 22, 1995, pp. 139-144, XP004041967.
Database UniProt [online] Oct. 1, 1996, "Fumarate Hydratase, Mitochondrial Precursor (EC 4.2.1.2) (Fumarase)." XP002477029.
De Jongh "Organic Acid Production by Aspergillus Niger", PHD Thesis, May 2006, pp. 1-109, XP002445685.
Song et al., "Production of Succinic Acid by Bacterial Fermentation", Enzyme and Microbial Technology, vol. 39, No. 3, Jul. 3, 2006, pp. 352-361, XP005459365.
Co-pending U.S. Appl. No. 12/743,416, filed May 18, 2010; WO 2009/065777.
Co-pending U.S. Appl. No. 12/743,106, filed May 14, 2010; WO 2009/065778.
Co-pending U.S. Appl. No. 12/743,927, filed May 20, 2010; WO 2009/0657808.
International Search Report for PCT/EP2008/065582, mailed Feb. 12, 2009.
International Search Report for PCT/EP2008/065583, mailed Feb. 12, 2009.
International Preliminary Report on Patentability for PCT/EP2008/065583, mailed Mar. 12, 2010.
International Search Report for PCT/EP2008/065588, mailed Feb. 12, 2009.
Written Opinion of the International Searching Authority, for PCT/EP2008/065588, mailed Feb. 12, 2009.
International Preliminary Report on Patentability for PCT/EP2008/065588, mailed Mar. 12, 2010.
Database UniProt [online], Apr. 12, 2005, "Mitochondrial NADH-Dependent Fumarate Reductase (EC 1.3.1.6)." XP002477927.
Database UniProt [online], Mar. 1, 2003, "NADH-Dependent Fumarate Reductase." XP002477928.
Database UniProt [Online], Accession No. A2R097, (Mar. 6, 2007), 2 pages. XP-002477243.
Database UniProt [Online], "Aspergillus niger contig An12c0260, complete genome.", Accession No. AM270282, (Jan. 28, 2007), 28 pages. XP-002477242.
Jacob et al.; "Fast High-Performance Liquid Chromatographic Purification of *Saccharomyces cerevisiae* Phosphoenolpyruvate Carboxykinase.", Journal of Chromatography, vol. 625, No. 1, Nov. 13, 1992, pp. 47-54, XP008091044.
Bauer et al.; "By-Product Formation during Exposure of Respiring *Saccharomyces cerevisiae* Cultures to Excess Glucose is not caused by a Limited Capacity of Pyruvate Carboxylase", FEMS Microbiology Letters, vol. 179, No. 1, Oct. 1, 1999, pp. 107-113, XP002478740.
Millard et al.; "Enhanced Production of Succinic Acid by Overexpression of Phosphoenolpyruvate Carboxylase in *Escherichia coli*", Applied and Environmental Microbiology, Washington, DC, US, vol. 62, No. 5, May 1, 1996, pp. 1808-1810, XP002132795.
Lin et al.; "Metabolic Engineering of Aerobic Succinate Production Systems in *Escherichia coli* to Improve Process Productivity and Achieve the Maximum Theoretical Succinate Yield", Metabolic Engineering, vol. 7, No. 2, Mar. 2005, pp. 116-127, XP004801711.
Kubo et al.; "Effect of Gene Disruption of Succinate Dehydrogenase on Succinate Production in a Sake Yeast Strain", Journal of Bioscience and Bioengineering, vol. 90, No. 6, 2000, pp. 619-624, XP003009625.
Coustou et al.; "A Mitochondrial NADH-dependent Fumarate Reductase Involved in the Production of Succinate Excreted by Procyclic Trypanosoma Brucei", Journal of Biological Chemistry, vol. 280, No. 17, Apr. 2005, pp. 16559-16570, XP002477924.
Enomoto et al.; "Physiolocial Role of Soluble Fumarate Recuctase in Redox Balancing during Anaerobiosis in *Saccharomyces cerevisiae*", FEMS Microbiology Letters, vol. 215, No. 1, Sep. 24, 2002, pp. 103-108, XP002477926.
Besteiro et al.; "Succinate Secreted by Trypanosoma Brucei is Produced by a Novel and Unique Glycosomal Enzyme, NADH-dependent Fumarate Reductase." Journal of Biological Chemistry, vol. 277, No. 41, Oct. 11, 2002, pp. 38001-38012, XP002477925.
U.S. Appl. No. 14/059,284, filed Oct. 21, 2013.
U.S. Appl. No. 14/044,722, filed Oct. 2, 2013.
U.S. Appl. No. 12/743,927, filed Sep. 15, 2010.
Nast et al., "Molecular Characterization of Potato Fumarate Hydratase and Functional Expression in *Escherichia coli*." Plant Physiol. (1996) 11 2: 121 9-1227.
Acuna et al., "Cloning, sequencing, and mutational analysis of the *Bradyrhizobium japonicum* fumC-like gene: evidence for the existence of two different fumarases." Journal of General Microbiology (1991), 137, 991-1000.
Gerbod et al., "Phylogenetic Relationships of Class II Fumarase Genes from *Trichomonad* Species." Mol. Biol. Evol. (2001)18(8):1574-1584.

\* cited by examiner

DICARBOXYLIC ACID PRODUCTION IN A RECOMBINANT YEAST

CROSS REFERENCE TO RELATED APPLICATIONS

This application is a Continuation Application of U.S. application Ser. No. 12/743,652, filed, May 19, 2010, which is a §371 National Stage Application of PCT/EP2008/065587, filed Nov. 14, 2008, which claims priority to European Application No. 07121117.1, filed Nov. 20, 2007, and European Application No. 08156960.0, filed May 27, 2008, the content of all of which are incorporated herein by reference in their entireties.

The present invention relates to a recombinant yeast comprising a nucleotide sequence encoding an enzyme that catalyses the conversion of malic acid to fumaric acid and a process for the production of a dicarboxylic acid.

Dicarboxylic acids, such as fumaric acid and succinic acid, are potential precursors for numerous chemicals. For example, succinic acid can be converted into 1,4-butanediol (BDO), tetrahydrofuran, and gamma-butyrolactone. Another product derived from succinic acid is a polyester polymer which is made by linking succinic acid and BDO.

Succinic acid is predominantly produced through petrochemical processes by hydrogenation of butane. These processes are considered harmful for the environment and costly. The fermentative production of succinic acid may be an attractive alternative process for the production of succinic acid, wherein renewable feedstock as a carbon source may be used.

A number of different bacteria such as *Escherichia coli*, and the rumen bacteria *Actinobacillus, Anaerobiospirillum, Bacteroides, Mannheimia*, or *Succinimonas* sp. are known to produce succinic acid. Metabolic engineering of these bacterial strains have improved the succinic acid yield and/or productivity, or reduced the by-product formation. WO2007/061590 discloses a pyruvate decarboxylase negative yeast for the production of malic acid and/or succinic acid which is transformed with a pyruvate carboxylase enzyme or a phosphoenolpyruvate carboxylase, a malate dehydrogenase enzyme, and a malic acid transporter protein (MAE).

Despite the improvements that have been made in the fermentative production of succinic acid, there remains a need for improved microorganisms for the fermentative production of succinic acid.

The aim of the present invention is an alternative yeast for the production of a dicarboxylic acid such as fumaric acid and succinic acid.

The aim is achieved according to the invention with a recombinant yeast comprising a nucleotide sequence encoding a heterologous enzyme that catalyses the conversion of malic acid to fumaric acid. Surprisingly it was found that an increased amount of dicarboxylic acid such as fumaric acid and/or succinic acid was produced by the recombinant yeast according to the present invention as compared to a wild-type yeast.

As used herein, a recombinant yeast according to the present invention is defined as a cell which contains, or is transformed or genetically modified with a nucleotide sequence and/or protein that does not naturally occur in the yeast, or it contains additional copy or copies of an endogenous nucleic acid sequence (or protein). A wild-type yeast is herein defined as the parental yeast of the recombinant yeast.

Preferably, the enzyme that catalyses the conversion of malic acid to fumaric acid is active in the cytosol upon expression of the nucleotide sequence encoding the enzyme.

An enzyme that catalyses the conversion of malic acid to fumaric acid, preferably has fumarase activity, preferably the enzyme is a fumarase of EC 4.2.1.2.

An enzyme that catalyses the conversion of malic acid to fumaric acid may be derived from any suitable origin, for instance bacteria, yeasts, fungi, protozoa or plants. Preferably, the enzyme according to the present invention is derived from *Rhizopus oryzae*.

It was shown that expression of a heterologous fumR gene of *Rhizopus oryzae* in *Aspergillus niger* did not result in succinic acid production under oxygen limited conditions (PhD thesis, 2006 W.A. de Jongh, Biocentrum Technical University of Denmark). Surprisingly, a yeast expressing a heterologous fumarase according to the present invention produced a higher amount of succinic acid under oxygen limited conditions as compared to the wild type yeast.

The term "homologous" when used to indicate the relation between a given (recombinant) nucleic acid or polypeptide molecule and a given host organism or host cell, is understood to mean that in nature the nucleic acid or polypeptide molecule is produced by a host cell or organisms of the same species, preferably of the same variety or strain.

The term "heterologous" when used with respect to a nucleic acid (DNA or RNA) or protein refers to a nucleic acid or protein that does not occur naturally as part of the organism, cell, genome or DNA or RNA sequence in which it is present, or that is found in a cell or location or locations in the genome or DNA or RNA sequence that differ from that in which it is found in nature. Heterologous nucleic acids or proteins are not endogenous to the cell into which it is introduced, but have been obtained from another cell or synthetically or recombinantly produced.

Preferably, the yeast according to the present invention is a yeast comprising a nucleotide sequence encoding an enzyme that catalyses conversion of malic acid to fumaric acid, wherein the enzyme has at least 70%, 75%, preferably at least 80, 85, 90, 92, 94, 95, 96, 97, 98, 99% sequence identity with the amino acid sequence of SEQ ID NO: 1, or SEQ ID NO: 3, preferably with the amino acid sequence of SEQ ID NO: 3, preferably the enzyme comprises SEQ ID NO:3.

Sequence identity is herein defined as a relationship between two or more amino acid (polypeptide or protein) sequences or two or more nucleic acid (polynucleotide) sequences, as determined by comparing the sequences. Usually, sequences are compared over the whole length of the sequences compared. In the art, "identity" also means the degree of sequence relatedness between amino acid or nucleic acid sequences, as the case may be, as determined by the match between strings of such sequences.

Preferred methods to determine identity are designed to give the largest match between the sequences tested. Methods to determine identity is codified in publicly available computer programs. Preferred computer program methods to determine identity between two sequences include BLASTP and BLASTN, publicly available from NCBI and other sources (BLAST Manual, Altschul, S., et al., NCBI NLM NIH Bethesda, Md. 20894). Preferred parameters for amino acid sequences comparison using BLASTP are gap open 11.0, gap extend 1, Blosum 62 matrix. Preferred parameters for nucleic acid sequences comparison using BLASTP are gap open 11.0, gap extend 1, DNA full matrix (DNA identity matrix).

A nucleotide sequence encoding an enzyme which catalyses the conversion of malic acid to fumaric acid in the cytosol according to the invention may also be defined by their capability to hybridise with the nucleotide sequences encoding the enzymes of SEQ ID NO: 1 or SEQ ID NO: 3, under moderate, or preferably under stringent hybridisation conditions. Stringent hybridisation conditions are herein defined as conditions that allow a nucleic acid sequence of at least about 25, preferably about 50 nucleotides, 75 or 100 and most preferably of about 200 or more nucleotides, to hybridise at a temperature of about 65° C. in a solution comprising about 1 M salt, preferably 6×SSC (sodium chloride, sodium citrate) or any other solution having a comparable ionic strength, and washing at 65° C. in a solution comprising about 0.1 M salt, or less, preferably 0.2×SSC or any other solution having a comparable ionic strength. Preferably, the hybridisation is performed overnight, i.e. at least for 10 hours and preferably washing is performed for at least one hour with at least two changes of the washing solution. These conditions will usually allow the specific hybridisation of sequences having about 90% or more sequence identity.

Moderate conditions are herein defined as conditions that allow a nucleic acid sequence of at least 50 nucleotides, preferably of about 200 or more nucleotides, to hybridise at a temperature of about 45° C. in a solution comprising about 1 M salt, preferably 6×SSC or any other solution having a comparable ionic strength, and washing at room temperature in a solution comprising about 1 M salt, preferably 6×SSC or any other solution having a comparable ionic strength. Preferably, the hybridisation is performed overnight, i.e. at least for 10 hours, and preferably washing is performed for at least one hour with at least two changes of the washing solution. These conditions will usually allow the specific hybridisation of sequences having up to 50% sequence identity. The person skilled in the art will be able to modify these hybridisation conditions in order to specifically identify sequences varying in identity between 50% and 90%.

The term "gene", as used herein, refers to a nucleic acid sequence containing a template for a nucleic acid polymerase, in eukaryotes, RNA polymerase II. Genes are transcribed into mRNAs that are then translated into protein.

The term "nucleic acid" as used herein, includes reference to a deoxyribonucleotide or ribonucleotide polymer, i.e. a polynucleotide, in either single- or double-stranded form, and unless otherwise limited, encompasses known analogues having the essential nature of natural nucleotides in that they hybridize to single-stranded nucleic acids in a manner similar to naturally occurring nucleotides (e.g., peptide nucleic acids). A polynucleotide can be full-length or a subsequence of a native or heterologous structural or regulatory gene. Unless otherwise indicated, the term includes reference to the specified sequence as well as the complementary sequence thereof.

The terms "polypeptide", "peptide" and "protein" are used interchangeably herein to refer to a polymer of amino acid residues. The terms apply to amino acid polymers in which one or more amino acid residue is an artificial chemical analogue of a corresponding naturally occurring amino acid, as well as to naturally occurring amino acid polymers. The essential nature of such analogues of naturally occurring amino acids is that, when incorporated into a protein, that protein is specifically reactive to antibodies elicited to the same protein but consisting entirely of naturally occurring amino acids. The terms "polypeptide", "peptide" and "protein" are also inclusive of modifications including, but not limited to, glycosylation, lipid attachment, sulfation, gamma-carboxylation of glutamic acid residues, hydroxylation and ADP-ribosylation.

The term "enzyme" as used herein is defined as a protein which catalyses a (bio)chemical reaction in a cell, such as a yeast cell.

To increase the likelihood that the introduced enzyme is expressed in active form in a yeast of the invention, the corresponding encoding nucleotide sequence may be adapted to optimise its codon usage to that of the chosen yeast cell. Several methods for codon optimisation are known in the art. A preferred method to optimise codon usage of the nucleotide sequences to that of the yeast is a codon pair optimization technology as disclosed in WO2008/000632. Codon-pair optimization is a method for producing a polypeptide in a host cell, wherein the nucleotide sequences encoding the polypeptide have been modified with respect to their codon-usage, in particular the codon-pairs that are used, to obtain improved expression of the nucleotide sequence encoding the polypeptide and/or improved production of the polypeptide. Codon pairs are defined as a set of two subsequent triplets (codons) in a coding sequence.

Usually, the nucleotide sequence encoding an enzyme, for instance the enzyme that catalyses the conversion of malic acid to fumaric acid, is operably linked to a promoter that causes sufficient expression of the corresponding nucleotide sequence in the yeast according to the present invention to confer to the yeast the ability to produce fumaric acid and/or succinic acid.

As used herein, the term "operably linked" refers to a linkage of polynucleotide elements (or coding sequences or nucleic acid sequence) in a functional relationship. A nucleic acid sequence is "operably linked" when it is placed into a functional relationship with another nucleic acid sequence. For instance, a promoter or enhancer is operably linked to a coding sequence if it affects the transcription of the coding sequence.

As used herein, the term "promoter" refers to a nucleic acid fragment that functions to control the transcription of one or more genes, located upstream with respect to the direction of transcription of the transcription initiation site of the gene, and is structurally identified by the presence of a binding site for DNA-dependent RNA polymerase, transcription initiation sites and any other DNA sequences known to a person skilled in the art. A "constitutive" promoter is a promoter that is active under most environmental and developmental conditions. An "inducible" promoter is a promoter that is active under environmental or developmental regulation.

A promoter that could be used to achieve the expression of a nucleotide sequence coding for an enzyme, such as an enzyme that catalyses the conversion of malic acid to fumaric acid, may be not native to the nucleotide sequence coding for the enzyme to be expressed, i.e. a promoter that is heterologous to the nucleotide sequence (coding sequence) to which it is operably linked. Preferably, the promoter is homologous, i.e. endogenous to the host cell.

Suitable promoters in this context include both constitutive and inducible natural promoters as well as engineered promoters, which are well known to the person skilled in the art. Suitable promoters in eukaryotic host cells may be GAL7, GAL10, or GAL 1, CYC1, HIS3, ADH1, PGL, PH05, GAPDH, ADC1, TRP1, URA3, LEU2, ENO, TPI, and AOX1. Other suitable promoters include PDC, GPD1, PGK1, TEF1, and TDH.

Usually a nucleotide sequence encoding an enzyme comprises a terminator. Any terminator, which is functional in the eukaryotic cell, may be used in the present invention. Preferred terminators are obtained from natural genes of the host cell. Suitable terminator sequences are well known in the art. Preferably, such terminators are combined with mutations that prevent nonsense mediated mRNA decay in the host cell of the invention (see for example: Shirley et al., 2002, Genetics 161:1465-1482).

In a preferred embodiment, the nucleotide sequence encoding an enzyme that catalyses the conversion of malic acid to fumaric acid, such as a fumarase, is overexpressed to achieve increased production of fumaric acid and/or succinic acid by a recombinant yeast according to the present invention.

There are various means available in the art for overexpression of nucleotide sequences encoding enzymes in the yeast cell of the invention. In particular, a nucleotide sequence encoding an enzyme may be overexpressed by increasing the copy number of the gene coding for the enzyme in the cell, e.g. by integrating additional copies of the gene in the cell's genome, by expressing the gene from a centromeric vector, from an episomal multicopy expression vector or by introducing an (episomal) expression vector that comprises multiple copies of the gene. Preferably, overexpression of the enzyme according to the invention is achieved with a (strong) constitutive promoter.

The nucleic acid construct may be a plasmid, for instance a low copy plasmid or a high copy plasmid. The yeast according to the present invention may comprise a single, but preferably comprises multiple copies of the nucleotide sequence encoding a fumarase, for instance by multiple copies of a nucleotide construct.

The nucleic acid construct may be maintained episomally and thus comprise a sequence for autonomous replication, such as an autosomal replication sequence sequence. A suitable episomal nucleic acid construct may e.g. be based on the yeast 2p or pKD1 plasmids (Gleer et al., 1991, Biotechnology 9: 968-975), or the AMA plasmids (Fierro et al., 1995, Curr Genet. 29:482-489). Alternatively, each nucleic acid construct may be integrated in one or more copies into the genome of the yeast cell. Integration into the cell's genome may occur at random by non-homologous recombination but preferably, the nucleic acid construct may be integrated into the cell's genome by homologous recombination as is well known in the art (see e.g. WO90/14423, EP-A-0481008, EP-A-0635 574 and U.S. Pat. No. 6,265, 186).

In a preferred embodiment an enzyme that catalyses the conversion of malic acid to fumaric acid is active in the cytosol upon expression of the encoding nucleotide sequence. Cytosolic activity of the enzyme is preferred for a high productivity of fumaric acid and/or succinic acid by the eukaryotic cell.

A nucleotide sequence encoding an enzyme that catalyses the conversion of malic acid to succinic acid, may comprise a peroxisomal or mitochondrial targeting signal, for instance as determined by the method disclosed by Schluter et al, Nucleic acid Research 2007, Vol 25, D815-D822. In the event the enzyme comprises a targeting signal, it may be preferred that the yeast according to the invention comprises a truncated form of the enzyme, wherein the targeting signal is removed.

The yeast according to the present invention preferably belongs to one of the genera *Saccharomyces*, *Pichia*, *Kluyveromyces*, or *Zygosaccharomyces*. More preferably, the eukaryotic cell is a *Saccharomyces cerevisiae*, *Saccharomyces uvarum*, *Saccharomyces bayanus*, *Pichia stipidis*, *Kluyveromyces marxianus*, *K. lactis*, *K. thermotolerans*, or *Zygosaccharomyces bailii*.

Preferably the yeast is a *Saccharomyces cerevisiae*, preferably a *Saccharomyces cerevisiae* comprising SEQ ID NO: 4.

In addition to a nucleotide sequence encoding an enzyme that catalyses the conversion of malic acid to fumaric acid according to the present invention, the recombinant yeast according to the present invention may comprise further genetic modifications, for instance mutations, deletions or disruptions, in homologous nucleotide sequences and/or transformation with nucleotide sequences that encode homologous or heterologous enzymes that catalyse a reaction in the cell resulting in an increased flux towards fumaric acid and/or succinic acid. It may for example be favorable to introduce, genetically modify and/or overexpress heterologous and/or homologous nucleotide sequences encoding i) an enzyme that catalyses the conversion of phosphoenolpyruvate or pyruvate to oxaloacetate; ii) a malate dehydrogenase that catalyses the conversion from oxaloacetate to malic acid; or iii) a fumarate reductase, which catalyses the conversion of fumaric acid to succinic acid. Preferably, the enzymes under i), ii) and iii) are expressed in the cytosol. Cytosolic expression may be achieved by deletion or modification of a mitochondrial or peroxisomal targeting signal as has been described herein before. Further molecular DNA techniques as described herein above, such as overexpression and codon optimization are also applicable to these nucleotide sequences.

The yeast may be transformed or genetically modified with any suitable nucleotide sequence catalyzing the reaction from a C3 to C4 carbon molecule, such as phosphoenolpyruvate (PEP, C3) to oxaloacetate (OAA,C4) and pyruvate (C3) to OAA or malic acid. Suitable enzymes are PEP carboxykinase (EC 4.1.1.49, EC 4.1.1.38) and PEP carboxylase (EC 4.1.1.31) which catalyse the conversion of PEP to OAA; pyruvate carboxylase (EC 6.4.1.1.), that catalyses the reaction from pyruvate to OAA; or malic enzyme (EC 1.1.1.38), that catalyses the reaction from pyruvate to malic acid.

Preferably, the activity of endogenous fumarase in the yeast according to the present invention is reduced, for instance by deletion, disruption or mutation of the gene encoding the endogenous fumarase of the yeast.

In another preferred embodiment the cell according to the present invention further comprises a homologous or heterologous malate dehydrogenase (MDH). Preferably, the activity of malate dehyodrogenase is increased by overexpression by known methods in the art as described herein. Preferably the MDH is expressed in the cytosol for instance as described in WO2007/061590

Preferably the yeast according to the present invention is a yeast wherein at least one gene encoding alcohol dehydrogenase is not functional. An alcohol dehydrogenase that is not functional is used herein to describe a yeast, wherein a gene encoding alcohol dehydrogenase is inactivated by mutation, disruption, or deletion, for instance by the method disclosed by Gueldener et. al. 2002, Nucleic Acids Research, Vol. 30, No. 6, e23. Preferably, the yeast is a *Saccharomyces cerevisiae*, wherein one or more genes adh1 and/or adh2, encoding alcohol dehydrogenase are inactivated.

Preferably the yeast according to the present invention further comprises at least one gene encoding glycerol-3-phosphate dehydrogenase which is not functional. A glycerol-3-phosphate dehydrogenase that is not functional is used herein to describe a yeast cell, wherein a gene encoding glycerol-3-phosphate dehydrogenase is inactivated by mutation, disruption, or deletion, resulting in a decreased formation of glycerol as compared to the wild-type yeast.

In a preferred embodiment, the yeast according to the present invention may be able to grow on any suitable carbon source known in the art and convert it to a dicarboxylic acid such as fumaric acid and/or succinic acid. The yeast may be able to convert directly plant biomass, celluloses, hemicelluloses, pectines, rhamnose, galactose, fructose, maltose, maltodextrines, ribose, ribulose, or starch, starch derivatives, sucrose, lactose and glycerol. Hence, a preferred yeast cell expresses enzymes such as cellulases (endocellulases and exocellulases) and hemicellulases (e.g. endo- and exo-xylanases, arabinases) necessary for the conversion of cellulose into glucose monomers and hemicellulose into xylose and arabinose monomers, pectinases able to convert pectines into glucuronic acid and galacturonic acid or amylases to convert starch into glucose monomers. The ability of a yeast to express such enzymes may be naturally present or may have been obtained by genetic modification of the yeast. Preferably, the yeast is able to convert a carbon source selected from the group consisting of glucose, fructose, galactose, xylose, arabinose, sucrose, lactose, raffinose and glycerol.

In another aspect, the present invention relates to a process for the preparation of a dicarboxylic acid, selected from fumaric acid and succinic acid, comprising fermenting the yeast according to the present invention in the presence of a suitable fermentation medium. Suitable fermentation media are known to the skilled man in the art. Preferably, the dicarboxylic acid produced in the process according to the present invention is succinic acid.

It was found advantageous to use a yeast according to the invention in the process for the production of a dicarboxylic acid, selected from fumaric acid and succinic acid, because a higher amount of succinic acid and/or fumaric acid was produced as compared to a wild type yeast. Preferably a yeast according to the present invention produces at least 1.1, preferably at least 1.2, 1.3, 1.4 1.5 or at least 2 times more succinic acid and/or fumaric acid as compared to a wild type yeast.

The process according to the present invention may be run under aerobic and anaerobic conditions. Preferably, the process is carried out under anaerobic conditions or under micro-aerophilic or oxygen limited conditions. An anaerobic fermentation process is herein defined as a fermentation process run in the absence of oxygen or in which substantially no oxygen is consumed, preferably less than 5, 2.5 or 1 mmol/L/h, and wherein organic molecules serve as both electron donor and electron acceptors.

An oxygen-limited fermentation process is a process in which the oxygen consumption is limited by the oxygen transfer from the gas to the liquid. The degree of oxygen limitation is determined by the amount and composition of the ingoing gasflow as well as the actual mixing/mass transfer properties of the fermentation equipment used. Preferably, in a process under oxygen-limited conditions, the rate of oxygen consumption is at least or about 5.5, more preferably at least or about 6 and even more preferably at least or about 7 mmol/L/h.

The process for the production of a dicarboxylic acid according to the present invention may be carried out at any suitable pH between 1 and 9. Preferably, the pH in the fermentation broth is between 2 and 7, preferably between 3 and 5. It was found advantageous to be able to carry out the process according to the present invention at a low pH, since this prevents bacterial contamination. In addition, since the pH drops during fumaric acid and/or succinic acid production, a lower amount of titrant is needed to keep the pH at a desired level.

A suitable temperature at which the process according to the present invention may be carried out is between 5 and 60° C., preferably between 10 and 50° C., more preferably between 15 and 35° C., more preferably between 18° C. and 30° C. The skilled man in the art knows which optimal temperatures are suitable for fermenting a specific yeast cell.

Preferably, the dicarboxylic acid, such as fumaric acid and succinic acid is recovered from the fermentation broth by a suitable method known in the art, for instance by crystallisation or ammonium precipitation.

Preferably, the dicarboxylic acid that is prepared in the process according to the present invention is further converted into a desirable product, such as a pharmaceutical, cosmetic, food, feed or chemical product. In case succinic acid is produced, succinic acid may be further converted into a polymer, such as polybutylene succinate (PBS) or other suitable polymers derived therefrom.

Genetic Modifications

Standard genetic techniques, such as overexpression of enzymes in the host cells, genetic modification of host cells, or hybridisation techniques, are known methods in the art, such as described in Sambrook and Russel (2001) "Molecular Cloning: A Laboratory Manual ($3^{rd}$ edition), Cold Spring Harbor Laboratory, Cold Spring Harbor Laboratory Press, or F. Ausubel et al, eds., "Current protocols in molecular biology", Green Publishing and Wiley Interscience, New York (1987). Methods for transformation, genetic modification etc of fungal host cells are known from e.g. EP-A-0 635 574, WO 98/46772, WO 99/60102 and WO 00/37671, WO90/14423, EP-A-0481008, EP-A-0635 574 and U.S. Pat. No. 6,265,186.

The following examples are for illustrative purposes only and are not to be construed as limiting the invention.

EXAMPLES

Example 1

Cloning of Fumarase from *Rhizopus* Oryzae in *Saccharomyces cerevisiae* Using *E. Coli* DH10B as Cloning Vehicle 1.1. Expression Constructs Fumarase [E.C. 4.2.1.2], GenBank accession number 469103, from *Rhizopus oryzae* was analysed for the presence of signal sequences using SignalP 3.0 (http://www.cbs.dtu.dk/services/SignalP/) Bendtsen, J. et al. (2004) Mol. Biol., 340:783-795 and TargetP 1.1 (http://www.cbs.dtu.dk/services/TargetP/) Emanuelsson, O. et al. (2007) Nature Protocols 2, 953-971.

Figure 1:
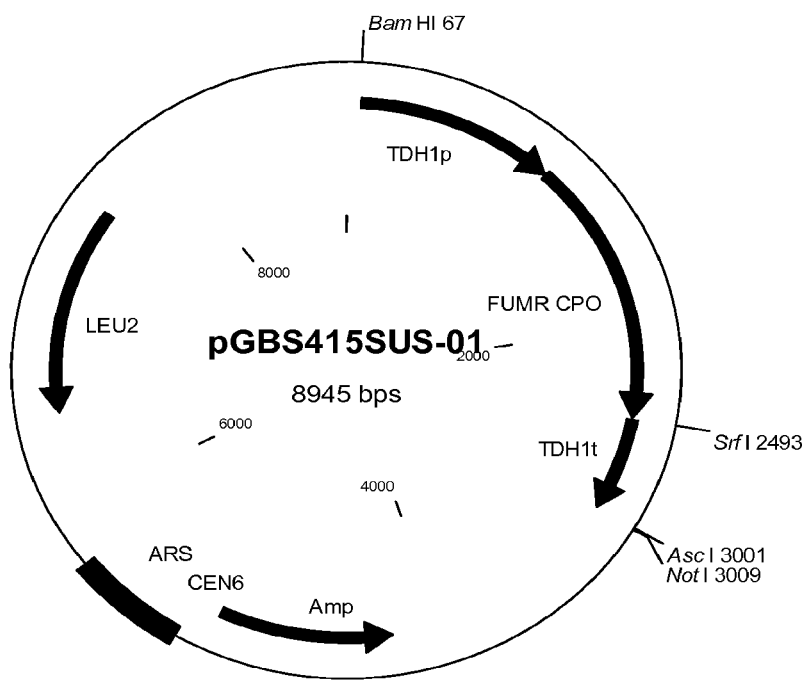
FIG. 1: Plasmid map of pGBS415SUS-01, encoding fumarase from *Rhizopus oryzae* for expression in *Saccharomyces cerevisiae*. CPO denotes codon pair optimized.
Figure 2:
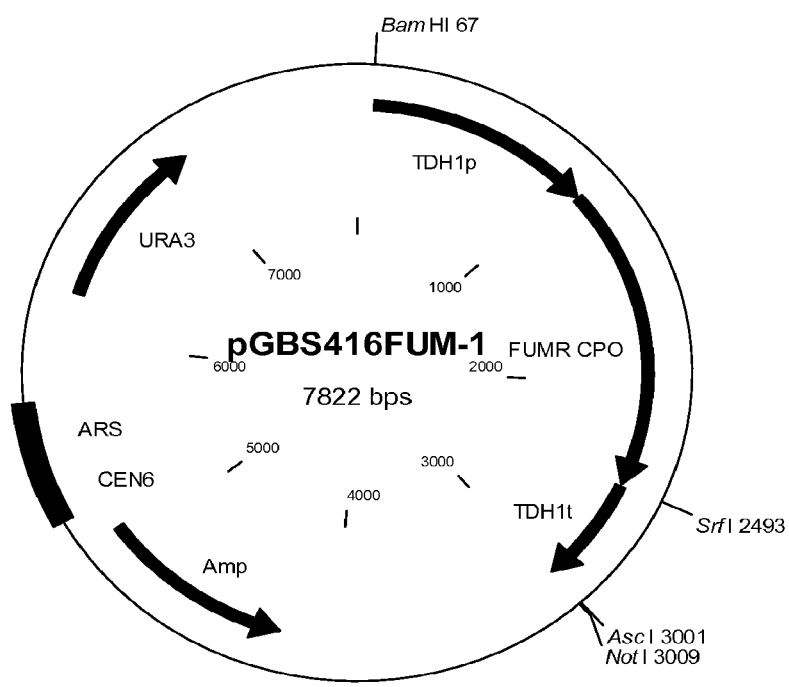
FIG. 2: Plasmid map of pGBS416FUM-1, encoding fumarase from *Rhizopus oryzae* for expression in *Saccharomyces cerevisiae*. CPO denotes codon pair optimized.

A putative mitochondrial targeting sequence in the first 23 amino acid of the protein was identified. To avoid potential targeting to mitochondria in *S. cerevisiae*, the first 23 amino acids were removed from SEQ ID NO: 1 (SEQ ID NO: 2 is corresponding nucleotide sequence) and a methionine amino acid was reintroduced, which resulted in SEQ ID NO: 3. SEQ ID NO: 3 was subjected to the codon-pair method as disclosed in PCT/EP2007/05594 for *S. cerevisiae*. The resulting sequence SEQ ID NO: 4 was put behind the constitutive TDH1 promoter sequence SEQ ID NO: 5 and before the TDH1 terminator sequence SEQ ID NO: 6, and convenient restriction sites were added. The stop codon in SEQ ID NO: 4 was modified into TAAG. The resulting sequence was synthesised at Sloning (Puchheim, Germany). The expression construct pGBS415SUS-01 was created after a BamHI/NotI restriction of the *S. cerevisiae* expression vector pRS415 (Sirkoski R. S. and Hieter P, Genetics, 1989, 122(1):19-27) and subsequently ligating in this vector a BamHI/NotI restriction fragment consisting of the fumarase (origin *Rhizopus oryzae*) synthetic gene construct (FIG. 1). The ligation mix is used for transformation of *E. coli* DH10B (Invitrogen) resulting in the yeast expression construct pGBS415SUS-01 (FIG. 1).

The construct pGBS415SUS-01 is transformed into *S. cerevisiae* strains CEN.PK113-6B (MATA ura3-52 leu2-112 trp1-289), RWB066 (MATA ura3-52 leu2-112 trp1-289 adh1::lox adh2::Kanlox) and RWB064 (MATA ura3-52 leu2-112 trp1-289 adh1::lox adh2::lox gpd1::Kanlox). Transformation mixtures are plated on Yeast Nitrogen Base (YNB) w/o AA (Difco)+2% glucose supplemented with appropriate amino acids. Transformants are inoculated in Verduyn medium comprising glucose supplemented with appropriate amino acids (Verduyn et al., 1992, Yeast. July; 8(7):501-17) and grown under aerobic, anaerobic and oxygen-limited conditions in shake flasks. The medium for anaerobic cultivation is supplemented with 0.01 g/l ergosterol and 0.42 g/l Tween 80 dissolved in ethanol (Andreasen and Stier, 1953, J. Cell. Physiol, 41, 23-36; Andreasen and Stier, 1954, J. Cell. Physiol, 43: 271-281). All yeast cultures are grown at 30° C. in a shaking incubator at 250-280 rpm. At different incubation times, aliquots of the cultures were removed, centrifuged and the medium is analysed by HPLC for formation of oxalic acid, malic acid, fumaric acid and succinic acid as described below.

1.2 HPLC Analysis

HPLC is performed for the determination of organic acids and sugars in different kinds of samples. The principle of the separation on a Phenomenex Rezex-RHM-Monosaccharide column is based on size exclusion, ion-exclusion and ion-exchange using reversed phase mechanisms. Detection takes place by differential refractive index and ultra violet detectors.

The invention claimed is:

1. A recombinant yeast comprising a nucleotide sequence encoding a heterologous fumarase of EC 4.2.1.2, wherein the heterologous fumarase is active in the cytosol upon expression of the nucleotide sequence, and wherein said recombinant yeast is capable of producing an increased amount of a dicarboxylic acid as compared to a wild-type yeast, wherein said dicarboxylic acid is selected from fumaric acid and succinic acid.

2. The recombinant yeast of claim 1, wherein the heterologous fumarase of EC 4.2.1.2 is derived from *Rhizopus oryzae*.

3. The recombinant yeast of claim 1, wherein the heterologous fumarase of EC 4.2.1.2 is derived from bacteria, yeast, fungi, protozoa or plants.

4. The recombinant yeast of claim 1, wherein the heterologous fumarase of EC 4.2.1.2 has at least 70% identity to SEQ ID NO:1 or SEQ ID NO:3.

5. The recombinant yeast of claim 1, which belongs to one of the genera *Saccharomyces, Pichia, Kluyveromyces*, or *Zygosaccharomyces*.

6. The recombinant yeast of claim 1, which is a *Saccharomyces cerevisiae* comprising SEQ ID NO:4.

7. A process for the production of a dicarboxylic acid selected from fumaric acid and succinic acid, which comprises fermenting a recombinant yeast comprising a nucleotide sequence encoding a heterologous fumarase of EC 4.2.1.2, wherein the heterologous fumarase is active in the cytosol upon expression of the nucleotide sequence, and wherein said recombinant yeast is capable of producing an increased amount of said dicarboxylic acid as compared to a wild-type yeast.

8. The process of claim 7, wherein the dicarboxylic acid is further converted into a pharmaceutical, cosmetic, food, feed, or chemical product.

9. The process of claim 7, wherein said heterologous fumarase of EC 4.2.1.2 is derived from bacteria, yeast, fungi, protozoa or plants.

10. The process of claim 7, wherein the increase is at least 1.1 times greater as compared to a wild-type yeast.

11. The process of claim 7, wherein said recombinant yeast belongs to one of the genera *Saccharomyces, Pichia, Kluyveromyces*, or *Zygosaccharomyces*.

12. The process of claim 11, wherein said recombinant yeast is a Saccharomyces cerevisiae comprising SEQ ID NO: 4.

13. The process of claim 7, wherein said heterologous fumarase of EC 4.2.1.2 has at least 70% sequence identity to SEQ ID NO:1 or SEQ ID NO:3.

14. The process of claim 7, wherein said heterologous fumarase of EC 4.2.1.2 has at least 75% sequence identity to SEQ ID NO:1 or SEQ ID NO:3.

15. The process of claim 7, wherein said heterologous fumarase of EC 4.2.1.2 has at least 80% sequence identity to SEQ ID NO:1 or SEQ ID NO:3.

16. The process of claim 7, wherein said heterologous fumarase of EC 4.2.1.2 is derived from fungi.

* * * * *

SEQUENCE LISTING

```
<160> NUMBER OF SEQ ID NOS: 6

<210> SEQ ID NO 1
<211> LENGTH: 494
<212> TYPE: PRT
<213> ORGANISM: Rhizopus oryzae

<400> SEQUENCE: 1

Met Leu Arg Ala Ser Ala Thr Arg Phe Leu Ser Gln Ala Lys Asn Met
1               5                   10                  15

Asn Asn Ser Pro Arg Leu Phe Ser Ser Ala Ser Ala Ala Leu Gln Lys
            20                  25                  30

Phe Arg Ala Glu Arg Asp Thr Phe Gly Asp Leu Gln Val Pro Ala Asp
        35                  40                  45

Arg Tyr Trp Gly Ala Gln Thr Gln Arg Ser Leu Gln Asn Phe Asp Ile
    50                  55                  60

Gly Gly Pro Thr Glu Arg Met Pro Glu Pro Leu Ile Arg Ala Phe Gly
65                  70                  75                  80

Val Leu Lys Lys Ala Ala Ala Thr Val Asn Met Thr Tyr Gly Leu Asp
                85                  90                  95

Pro Lys Val Gly Glu Ala Ile Gln Lys Ala Ala Asp Glu Val Ile Asp
            100                 105                 110

Gly Ser Leu Ile Asp His Phe Pro Leu Val Val Trp Gln Thr Gly Ser
        115                 120                 125

Gly Thr Gln Thr Lys Met Asn Val Asn Glu Val Ile Ser Asn Arg Ala
    130                 135                 140

Ile Glu Leu Leu Gly Gly Glu Leu Gly Ser Lys Ala Pro Val His Pro
145                 150                 155                 160

Asn Asp His Val Asn Met Ser Gln Ser Ser Asn Asp Thr Phe Pro Thr
                165                 170                 175

Ala Met His Val Ala Ala Val Val Glu Ile His Gly Arg Leu Ile Pro
            180                 185                 190

Ala Leu Thr Thr Leu Arg Asp Ala Leu Gln Ala Lys Ser Ala Glu Phe
        195                 200                 205
```

```
Glu His Ile Ile Lys Ile Gly Arg Thr His Leu Gln Asp Ala Thr Pro
    210                 215                 220
Leu Thr Leu Gly Gln Glu Phe Ser Gly Tyr Thr Gln Gln Leu Thr Tyr
225                 230                 235                 240
Gly Ile Ala Arg Val Gln Gly Thr Leu Glu Arg Leu Tyr Asn Leu Ala
                245                 250                 255
Gln Gly Gly Thr Ala Val Gly Thr Gly Leu Asn Thr Arg Lys Gly Phe
                260                 265                 270
Asp Ala Lys Val Ala Glu Ala Ile Ala Ser Ile Thr Gly Leu Pro Phe
            275                 280                 285
Lys Thr Ala Pro Asn Lys Phe Glu Ala Leu Ala Ala His Asp Ala Leu
    290                 295                 300
Val Glu Ala His Gly Ala Leu Asn Thr Val Ala Cys Ser Leu Met Lys
305                 310                 315                 320
Ile Ala Asn Asp Ile Arg Tyr Leu Gly Ser Gly Pro Arg Cys Gly Leu
                325                 330                 335
Gly Glu Leu Ser Leu Pro Glu Asn Glu Pro Gly Ser Ser Ile Met Pro
                340                 345                 350
Gly Lys Val Asn Pro Thr Gln Cys Glu Ala Met Thr Met Val Cys Ala
            355                 360                 365
Gln Val Met Gly Asn Asn Thr Ala Ile Ser Val Ala Gly Ser Asn Gly
    370                 375                 380
Gln Phe Glu Leu Asn Val Phe Lys Pro Val Met Ile Lys Asn Leu Ile
385                 390                 395                 400
Gln Ser Ile Arg Leu Ile Ser Asp Ala Ser Ile Ser Phe Thr Lys Asn
                405                 410                 415
Cys Val Val Gly Ile Glu Ala Asn Glu Lys Lys Ile Ser Ser Ile Met
                420                 425                 430
Asn Glu Ser Leu Met Leu Val Thr Ala Leu Asn Pro His Ile Gly Tyr
            435                 440                 445
Asp Lys Ala Ala Lys Cys Ala Lys Lys Ala His Lys Glu Gly Thr Thr
    450                 455                 460
Leu Lys Glu Ala Ala Leu Ser Leu Gly Tyr Leu Thr Ser Glu Glu Phe
465                 470                 475                 480
Asp Gln Trp Val Arg Pro Glu Asp Met Ile Ser Ala Lys Asp
                485                 490
```

<210> SEQ ID NO 2
<211> LENGTH: 1419
<212> TYPE: DNA
<213> ORGANISM: Rhizopus oryzae

<400> SEQUENCE: 2

| | | |
|---|---|---|
| atgagtagtg cctctgctgc tttgcaaaaa ttccgtgctg agcgcgatac ttttggtgat | 60 |
| ctccaagttc ctgctgatag atattggggt gctcaaaccc aaaggtctct tcaaaatttt | 120 |
| gacattggtg gccctactga acgtatgccc gaacctttga tccgtgcctt tggtgtcctc | 180 |
| aaaaaggctg ctgctactgt caacatgact tatggcttgg atcctaaagt tggtgaagct | 240 |
| attcaaaagg ctgctgacga ggtcattgat ggaagcttga ttgatcattt ccctcttgtt | 300 |
| gtctggcaaa ctggttccgg tactcaaacc aagatgaacg ttaacgaagt tatctccaac | 360 |
| cgtgctattg aactttttggg tggtgagctt ggtagtaagg ctcctgttca tcccaacgat | 420 |
| catgtcaaca tgagtcaatc atccaatgac acgttcccta ctgccatgca cgttgctgct | 480 |

```
gttgttgaaa ttcacggtcg acttattcct gctttgacca ctttgcgtga tgcccttcaa    540
gccaaatccg ctgagtttga acacatcatc aagatcggtc gtactcactt gcaagatgca    600
actcctttga ctctcggtca agaattctct ggttatactc aacaattgac ttacggtatt    660
gctcgtgtac aaggtaccct tggagcgcct c tataaccttg ctcaaggtgg tactgctgtt    720
ggtactggtc ttaacaccag aaaaggtttc gatgccaagg tagctgaagc tattgcttct    780
attaccggtc ttccttt caa gaccgcccct aataagtttg aagcccttgc tgctcacgat    840
gctctcgttg aagctcacgg agctctcaat accgttgctt gttctcttat gaagatcgcc    900
aacgatatcc gttatcttgg ttctggacct cgctgtggtc ttggtgaact ttccttgcct    960
gaaaacgaac ccggatcttc tatcatgccc ggtaaggtta atcctactca atgtgaagct   1020
atgaccatgg tctgtgctca agtcatgggt aacaacactg ctatttctgt tgctggttcc   1080
aatggtcaat tcgagcttaa tgtcttcaaa cccgtcatga tcaagaactt gatccaatcc   1140
attcgtctta tttctgatgc ctctatttca ttcaccaaaa actgtgttgt tggtattgaa   1200
gccaatgaaa agaagattag cagcattatg aatgagtcat tgatgttggt cactgctctt   1260
aaccctcata ttggttacga taaagctgct aaatgtgcca agaaggccca caaggaaggc   1320
accaccttga aggaagctgc cctttctctt ggttacttga cttctgaaga attcgaccag   1380
tgggttagac ccgaagatat gatctctgcc aaggattaa                         1419
```

```
<210> SEQ ID NO 3
<211> LENGTH: 472
<212> TYPE: PRT
<213> ORGANISM: Artificial Sequence
<220> FEATURE:
<223> OTHER INFORMATION: Fumarase R. oryzae minus putative targeting
      signal

<400> SEQUENCE: 3
```

Met Ser Ser Ala Ser Ala Leu Gln Lys Phe Arg Ala Glu Arg Asp
1               5                   10                  15

Thr Phe Gly Asp Leu Gln Val Pro Ala Asp Arg Tyr Trp Gly Ala Gln
            20                  25                  30

Thr Gln Arg Ser Leu Gln Asn Phe Asp Ile Gly Gly Pro Thr Glu Arg
        35                  40                  45

Met Pro Glu Pro Leu Ile Arg Ala Phe Gly Val Leu Lys Lys Ala Ala
    50                  55                  60

Ala Thr Val Asn Met Thr Tyr Gly Leu Asp Pro Lys Val Gly Glu Ala
65                  70                  75                  80

Ile Gln Lys Ala Ala Asp Glu Val Ile Asp Gly Ser Leu Ile Asp His
                85                  90                  95

Phe Pro Leu Val Val Trp Gln Thr Gly Ser Gly Thr Gln Thr Lys Met
            100                 105                 110

Asn Val Asn Glu Val Ile Ser Asn Arg Ala Ile Glu Leu Leu Gly Gly
        115                 120                 125

Glu Leu Gly Ser Lys Ala Pro Val His Pro Asn Asp His Val Asn Met
    130                 135                 140

Ser Gln Ser Ser Asn Asp Thr Phe Pro Thr Ala Met His Val Ala Ala
145                 150                 155                 160

Val Val Glu Ile His Gly Arg Leu Ile Pro Ala Leu Thr Thr Leu Arg
                165                 170                 175

Asp Ala Leu Gln Ala Lys Ser Ala Glu Phe Glu His Ile Ile Lys Ile
            180                 185                 190

Gly Arg Thr His Leu Gln Asp Ala Thr Pro Leu Thr Leu Gly Gln Glu
            195                 200                 205

Phe Ser Gly Tyr Thr Gln Leu Thr Tyr Gly Ile Ala Arg Val Gln
    210                 215                 220

Gly Thr Leu Glu Arg Leu Tyr Asn Leu Ala Gln Gly Gly Thr Ala Val
225                 230                 235                 240

Gly Thr Gly Leu Asn Thr Arg Lys Gly Phe Asp Ala Lys Val Ala Glu
                245                 250                 255

Ala Ile Ala Ser Ile Thr Gly Leu Pro Phe Lys Thr Ala Pro Asn Lys
            260                 265                 270

Phe Glu Ala Leu Ala Ala His Asp Ala Leu Val Glu Ala His Gly Ala
        275                 280                 285

Leu Asn Thr Val Ala Cys Ser Leu Met Lys Ile Ala Asn Asp Ile Arg
    290                 295                 300

Tyr Leu Gly Ser Gly Pro Arg Cys Gly Leu Gly Glu Leu Ser Leu Pro
305                 310                 315                 320

Glu Asn Glu Pro Gly Ser Ser Ile Met Pro Gly Lys Val Asn Pro Thr
                325                 330                 335

Gln Cys Glu Ala Met Thr Met Val Cys Ala Gln Val Met Gly Asn Asn
            340                 345                 350

Thr Ala Ile Ser Val Ala Gly Ser Asn Gly Gln Phe Glu Leu Asn Val
        355                 360                 365

Phe Lys Pro Val Met Ile Lys Asn Leu Ile Gln Ser Ile Arg Leu Ile
    370                 375                 380

Ser Asp Ala Ser Ile Ser Phe Thr Lys Asn Cys Val Val Gly Ile Glu
385                 390                 395                 400

Ala Asn Glu Lys Lys Ile Ser Ser Ile Met Asn Glu Ser Leu Met Leu
                405                 410                 415

Val Thr Ala Leu Asn Pro His Ile Gly Tyr Asp Lys Ala Ala Lys Cys
            420                 425                 430

Ala Lys Lys Ala His Lys Glu Gly Thr Thr Leu Lys Glu Ala Ala Leu
        435                 440                 445

Ser Leu Gly Tyr Leu Thr Ser Glu Glu Phe Asp Gln Trp Val Arg Pro
    450                 455                 460

Glu Asp Met Ile Ser Ala Lys Asp
465                 470

<210> SEQ ID NO 4
<211> LENGTH: 1419
<212> TYPE: DNA
<213> ORGANISM: Artificial Sequence
<220> FEATURE:
<223> OTHER INFORMATION: nt FumR minus putative targeting codon
      optimised for S.cerevisae

<400> SEQUENCE: 4
atgtcctctg cttctgctgc tttgcaaaaa ttcagagctg aaagagatac cttcggtgac      60
ttgcaagttc cagctgaccg ttactggggt gctcaaactc aaagatcttt gcaaaacttt     120
gacattggtg gtccaactga agaatgcca gaaccattaa tcagagcttt cggtgttttg      180
aagaaggctg ctgccaccgt caacatgacc tacggtttgg acccaaaggt tggtgaagcc     240
atccaaaagg ctgctgacga agttatcgat ggttctttga ttgaccattt cccattggtt     300
gtctggcaaa ccggttctgg tactcaaacc aagatgaacg tcaatgaagt catctccaac     360
agagccattg aattgttggg tggtgaatta ggttccaagg ctccagtcca cccaaacgat     420

```
catgtcaaca tgtctcaatc ttccaacgac actttcccaa ctgccatgca cgttgctgcc      480
gttgttgaaa ttcacggtag attgattcca gctttgacca ctttgagaga tgctttgcaa      540
gccaaatctg ctgaattcga acacatcatc aagattggta gaacccactt gcaagatgct      600
accccattga ctttaggtca agaattctcc ggttacactc aacaattgac ctacggtatt      660
gctcgtgttc aaggtacttt ggaaagatta tacaacttgg ctcaaggtgg tactgctgtc      720
ggtactggtt tgaacaccag aaagggtttc gatgccaagg ttgctgaagc cattgcttcc      780
atcactggtt taccattcaa gaccgctcca aacaaattcg aagctttggc tgctcacgac      840
gctttggttg aagctcacgg tgctttgaac accgttgctt gttctttgat gaagattgcc      900
aacgatatcc gttacttggg ttctggtcca agatgtggtt taggtgaatt gtctctacca      960
gaaaacgaac caggttcttc catcatgcca ggtaaggtca acccaactca atgtgaagct     1020
atgaccatgg tttgtgctca agtcatgggt aacaacactg ccatctctgt tgctggttcc     1080
aacggtcaat tcgaattgaa tgtctttaaa ccagtcatga tcaagaactt gatccaatcc     1140
atcagattaa tctctgacgc ttccatctct ttcaccaaga actgtgttgt cggtattgaa     1200
gctaacgaaa agaagatctc ctccatcatg aacgaatctt tgatgttggt cactgctttg     1260
aaccctcaca ttggttacga caaggctgcc aagtgtgcca agaaggctca caggaaggt      1320 accactttga agaagctgc tctatctttg ggttacttga cctctgaaga attcgaccaa     1380
tgggttagac ctgaggacat gatttctgcc aaggattaa                           1419

<210> SEQ ID NO 5
<211> LENGTH: 1000
<212> TYPE: DNA
<213> ORGANISM: Artificial Sequence
<220> FEATURE:
<223> OTHER INFORMATION: TDH1 promotor

<400> SEQUENCE: 5 cttcccttt  acagtgcttc ggaaaagcac agcgttgtcc aagggaacaa ttttcttca      60 agttaatgca taagaaatat ctttttttat gtttagctaa gtaaaagcag cttggagtaa     120
aaaaaaaaat gagtaaattt ctcgatggat tagtttctca caggtaacat aacaaaaacc     180
aagaaaagcc cgcttctgaa aactacagtt gacttgtatg ctaaagggcc agactaatgg     240
gaggagaaaa agaaacgaat gtatatgctc atttacactc tatatcacca tatggaggat     300
aagttgggct gagcttctga tccaattat tctatccatt agttgctgat atgtcccacc      360
agccaacact tgatagtatc tactcgccat tcacttccag cagcgccagt agggttgttg     420
agcttagtaa aaatgtgcgc accacaagcc tacatgactc cacgtcacat gaaaccacac     480
cgtggggcct tgttgcgcta ggaataggat atgcgacgaa gacgcttctg cttagtaacc     540
acaccacatt ttcaggggt cgatctgctt gcttccttta ctgtcacgag cggcccataa      600
tcgcgctttt tttttaaaag gcgcgagaca gcaacagga agctcgggtt tcaaccttcg      660
gagtggtcgc agatctggag actggatctt tacaatacag taaggcaagc caccatctgc     720
ttcttaggtg catgcgacgg tatccacgtg cagaacaaca tagtctgaag aaggggggga     780
ggagcatgtt cattctctgt agcagtaaga gcttggtgat aatgaccaaa actggagtct     840
cgaaatcata taaatagaca atatattttc acacaatgag atttgtagta cagttctatt     900
ctctctcttg cataaataag aaattcatca agaacttggt ttgatattc accaacacac      960 acaaaaaaca gtacttcact aaatttacac acaaaacaaa                          1000
```

<210> SEQ ID NO 6
<211> LENGTH: 500
<212> TYPE: DNA
<213> ORGANISM: Artificial Sequence
<220> FEATURE:
<223> OTHER INFORMATION: TDH1 terminator

<400> SEQUENCE: 6

```
ataaagcaat cttgatgagg ataatgattt tttttttgaat atacataaat actaccgttt      60
ttctgctaga ttttgtgaag acgtaaataa gtacatatta cttttttaagc caagacaaga    120 ttaagcatta actttacccct tttctcttct aagtttcaat actagttatc actgtttaaa    180
agttatggcg agaacgtcgg cggttaaaat atattaccct gaacgtggtg aattgaagtt    240
ctaggatggt ttaaagattt ttccttttttg ggaaataagt aaacaatata ttgctgcctt    300
tgcaaaacgc acatacccac aatatgtgac tattggcaaa gaacgcatta tcctttgaag    360
aggtggatac tgatactaag agagtctcta ttccggctcc acttttagtc cagagattac    420
ttgtcttctt acgtatcaga acaagaaagc atttccaaag taattgcatt tgcccttgag    480
cagtatatat atactaagaa                                                  500
```